United States Patent
Torch (10) Patent No.: US 6,246,344 B1
(45) Date of Patent: *Jun. 12, 2001

(54) METHOD AND APPARATUS FOR VOLUNTARY COMMUNICATION

(76) Inventor: William C. Torch, 75 Pringle Way, Suite 701, Reno, NV (US) 89502

(*) Notice: Subject to any disclaimer, the term of this patent is extended or adjusted under 35 U.S.C. 154(b) by 0 days.

This patent is subject to a terminal disclaimer.

(21) Appl. No.: 08/978,100

(22) Filed: Nov. 25, 1997

Related U.S. Application Data (63) Continuation-in-part of application No. 08/699,670, filed on Aug. 19, 1996, now Pat. No. 5,748,113.

(51) Int. Cl.[7] .................................................. H03K 17/94
(52) U.S. Cl. ............................ 341/21; 341/173; 340/575; 340/825.19; 607/7; 128/903
(58) Field of Search .............................. 341/21, 20, 173, 341/176; 340/575, 825.19, 576; 607/7, 6; 128/902, 903

(56) References Cited

U.S. PATENT DOCUMENTS

| 3,863,243 | * | 1/1975 | Skolnick et al. | 340/575 |
| 5,748,113 | * | 5/1998 | Torch | 341/21 |

* cited by examiner

Primary Examiner—Brian Zimmerman
Assistant Examiner—Timothy Edwards, Jr.
(74) Attorney, Agent, or Firm—Herbert C. Schulze (57) ABSTRACT

A method and apparatus for voluntary and involuntary communication by means of transmitting, receiving, interpreting, and displaying messages detected and generated by relative eyelid movement, particularly by using the differences in reflectivity of the human eye and eyelid to produce the messages.

6 Claims, 11 Drawing Sheets

METHOD AND APPARATUS FOR VOLUNTARY COMMUNICATION

CROSS REFERENCE TO RELATED PATENT APPLICATIONS

This application is related to, and is a continuation in part of my application Ser. No. 08/699,670, filed Aug. 19, 1996, U.S. Pat. No. 5,748,113.

BACKGROUND OF THE INVENTION

I. Field of the Invention

This invention is in the general field of methods and apparatus for communicating;

The invention is more particularly directed to a method and apparatus for silent communication;

The invention is even more particularly directed to a method and apparatus for using movement of a human eyelid to communicate messages;

The invention is even more particularly directed to a method of voluntary and involuntary communication of the physical, emotional and mental state of persons.

II. Description of the Prior Art

In the past there have been some attempts to use the human eyelid to detect drowsiness or the like. Examples of such devices are disclosed in U.S. Pat. Nos. 4,953,111; 4,836,219; 4,725,824; and 4,967,186.

I do know that there have been communication devices utilizing certain bodily functions for achieving the desired results. Examples of such communications are found in U.S. Pat. Nos. 3,925,779; 4,746,913; 4,408,192; 4,293,855; 4,298,863; 5,233,662; 3,986,030; and 4,109,145. Some of these involve the eye. U.S. Pat. No. 4,109.145 involves a line of sight apparatus directed toward predetermined positions and time; U.S. Pat. No. 3,986,030 involves light reflection of the eye to a number of keyboard sensors; U.S. Pat. No. 4,408,192 involves muscle movement of three muscles, including, possibly the eye; and U.S. Pat. No. 5,517,021 involves electrical signals generated by an individual in connection with eye movements.

There have been various other attempts to detect states of drowsiness and the like by measuring various eye movements.

However, to my knowledge there has never been an effective method to measure and, therefore, to respond to desired (or voluntary), as well as involuntary, communication of the needs of a person who has become disabled in some manner by reason of the reflectivity of the eye and the eyelid.

To my knowledge the present invention is totally novel and unique in that it uses the difference in reflectivity of the eye and the eyelid for a very easily understood method of communication which may be practiced by almost anyone. This is distinguished from all of the prior known art, including all of the above listed patents. The full extent of the distinguishing characteristics of the present invention will be clear upon a reading of the description of a preferred embodiment which follows.

SUMMARY OF THE INVENTION

There are many circumstances under which persons may lose their ability to speak or to write. Such circumstances include, without limitation, persons who have had severe strokes, certain types of brain injury, certain types of other injuries, and the like which leaves such persons with no ability to speak or to use their limbs for writing or the like. Many of such persons, for example those in intensive care, or the like, do have brain functioning such that they wish to communicate to others, and others may wish to seek responses concerning various matters, but which cannot be provided by such persons as have been described. Additionally, persons may temporarily lose their ability properly to communicate by reason of injury, unconsciousness, sleep deprivation, drugs or the like.

I have observed that most individuals who have severe disorders of the type mentioned do have control of their eyelids even though they may not have control of any essential muscles, even including muscles that move their eyes.

Therefore, I have now conceived and perfected a method and apparatus which enables persons with disabilities as described to communicate with others willfully, involuntarily or unknowingly through the use of eyelid motion.

I have accomplished this by electronically sensing eyelid motion and converting this sensing of the eyelid motion into actual audible or visible messages. For example, in the simplest of terms a short blink of the eyelid can be used to indicate a dot and a long blink of the eyelid a dash, and then a person can communicate using dots and dashes as in the Morse Code, or to indicate zeros and ones in a binary code, and the like.

After having developed the method and apparatus which will described in more detail below, I discovered other uses which are not confined to disabled persons.

For example, my method and apparatus can be utilized as a silent alarm system by such persons as 1) bank tellers, police, and the like to communicate warnings during the commission of a crime or the like; 2) by the elderly person or epileptic individual who may have fainted, blacked out (epilepsy episode or the like), or is having a seizure epileptic episode or the like), or other emergency event. Its application include use as a: a) personal alarm and monitoring system; b) communication device; c) medical diagnostic biosensor; d) research biosensor; e) bio feed back device; f) security and military device; g) control device; h) educational device and toy.

Very importantly, my method and apparatus may now be used for a very comprehensive and important communication and diagnostic tool. As examples, my method and apparatus may be used for conscious communication by a totally disabled person. For example, well known French Author Jean Dominique Bauby describes his "locked-in" stroke in Reader's Digest October 1997 ("in the Blink of an eye"). It takes little imagination how he could have exemplified upon his marvelous story if he had had my invention to work with.

Additionally, my invention allows for monitoring an individual's emotional, mental, and physical states without any conscious response, or even knowledge that such monitoring is occurring.

My invention, thus becomes a total, and totally new and unique, method of communication, not only for communication in general, but to communicate the needs and desires, the physical and emotional state, and all other aspects of normal communication between one impaired and others. Importantly, it is not important that the communicator (the disabled, drowsy, semi-conscious, or otherwise totally, partially, voluntarily, involuntarily, or otherwise, incommunicative) even know he/she is communicating.

The normal eye blink lasts 0.1 to 0.2 second. The apparatus I have developed to perform this method of communication can be fine tuned to a natural, or an unnatural blinking cycle. Of course, as previously mentioned a long blink and a short blink can be consciously utilized to convey coded messages.

The method and apparatus of this invention operates by light emission and reflection, taking advantage of different reflectiveness of the eye lid, the eye globe, pupil, etc. Fortunately, what I have developed does not respond to skin color. Thus the racial background of the individual will not be any cause for concern in using this invention.

Furthermore, ambient lighting conditions do not affect the operation of this method and apparatus. Therefore, total absence of light, subdued or bright light, sunlight, flickering, etc. do not prevent the proper use of this invention. The light may be blocked by certain things such as mascara and may be intensified by such things as silver or the like.

Many states of physical and mental abnormality and the like can be monitored with this invention, as well as its use in communication (although, in effect, detecting the state of abnormality may be considered a form of communication). This invention can be used in connection with such conditions as epileptic seizures, drug side effects, sleep laboratory monitoring, monitoring the sleeping and waking states of children and others, demented persons of demented persons with Alzheimer's disease, patients intubated and on ventilators in hospital intensive care, prisoner state of consciousness, and the like. The eyelid communication system disclosed here can provide a steam of data about a person's state of wakefulness, sleepiness, and the like which can be integrated with data from sensors monitoring vehicles or machinery for safety purposes.

The motion of the eyelid as detected by my apparatus may be directed to computers which can convert the appropriate message and display it on a monitor, print it, forward it to another location by any appropriate means such as (without limitation) hard wire, electrical or electronic linkage, infrared, radio frequency signals, and the like.

It is an object of this invention to provide a method of communication utilizing the movement of an eyelid to generate a signal and convey messages, and to provide biofeedback. Similarly the signal may be used to take actions, such as ringing a bell, turning on a light, turning on an electrical appliance or motor "on or off" among other actions too numerous to list;

It is another object of this invention to provide such a method of communication wherein the communication can be confidential;

It is still a further object of this invention to provide such a method of communication as has been described wherein complete secrecy can be assured;

Another object is to provide a method for monitoring mental and physical states of individuals.

The foregoing and other objects and advantages of this invention will become apparent to those skilled in the art upon reading the description of a preferred embodiment which follows in conjunction with a review of the appended drawings.

DESCRIPTION OF A PREFERRED EMBODIMENT

Figure 1:
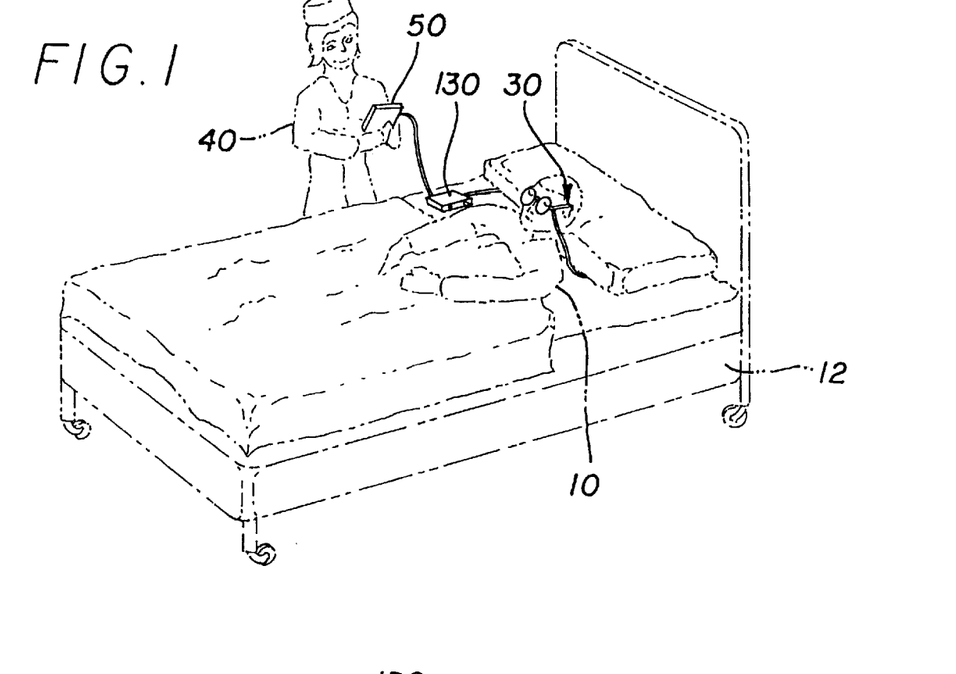
FIG. 1 is a perspective of a patient in a hospital using the apparatus of this invention to practice the method of this invention.

In FIG. 1, a patient 10 is in a hospital bed 12 wearing an eyeglass-like apparatus 20, which will detect whether the patient's eye is open or closed. Circuitry within box 130 will convert a code transmitted by the detector 30, depending upon a succession of openings and closing of the eyelid, to a message displayed on monitor 50, held and being read by nurse 40. Likewise, the information may be transmitted by direct wiring or by any indirect transmission such as radio frequency, infra-red, and the like to a computer, TV monitor, or the like.

Figure 2:
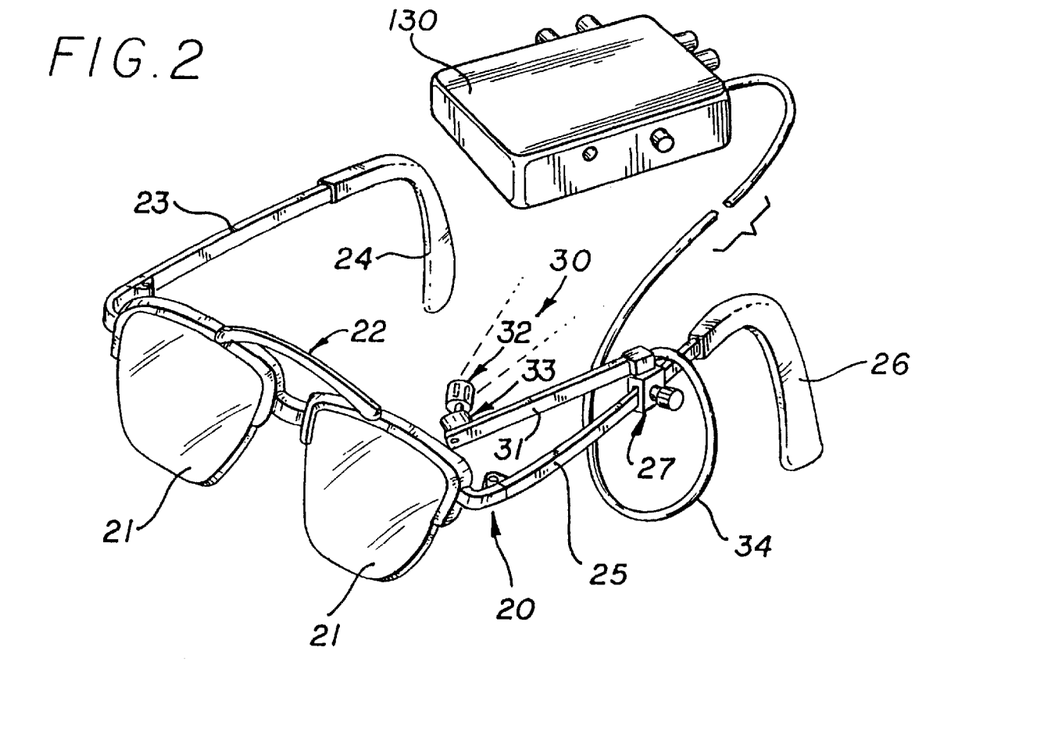
FIG. 2 is an enlarged perspective of the apparatus being used in FIG. 1.

FIG. 2 shows an eyeglass-like apparatus 20 which may be used to practice the method of this invention. A pair of lenses 21 are shown as is customary with eyeglasses. However, the lenses are not necessary. The bridgework 22 is like the bridgework of any eyeglasses. The side members 23 and 25 carry ear pieces 24 and 26 which will be worn as a pair of conventional glasses. Some type of clamping arrangement 27, which will be know to those skilled in the art, and which may be in various forms will be used to hold the sensing device 30, comprising sensor 32-emitter 33 on an adjustable arm 31. The signal received will be transmitted, by means known to those skilled in the art, through cables, or the like (also, known to those skilled in the art) 34, into processing box 130. It is to be understood that the sensor-emitter may be carried by, or be inserted in, the lens, the nasal bridge, etc. A single sensor/emitter may be placed near one eye, or a sensor/emitter may be placed near each eye. In this manner, the eyelid movement signals may be transmitted by one or both eyes in the form of binary, Morse code, or other signal system.

The processing box 130 will preferably contain all the electronic circuitry illustrated in all of the various diagrams. It may also contain circuitry which will be understood by those skilled in the art for various specialized purposes. Such purposes will have to do with transmission of data and conversion into various formats. For example, the transmission may be into pictorial representations, voice simulation, and the like. The technical aspects of all of these purposes, and the equipment to perform the necessary functions, are well known to those skilled in the art, and are in use in other applications, but have not heretofore been realized or utilized in connection with eyelid communication as herein described.

Figures 3, 3A:
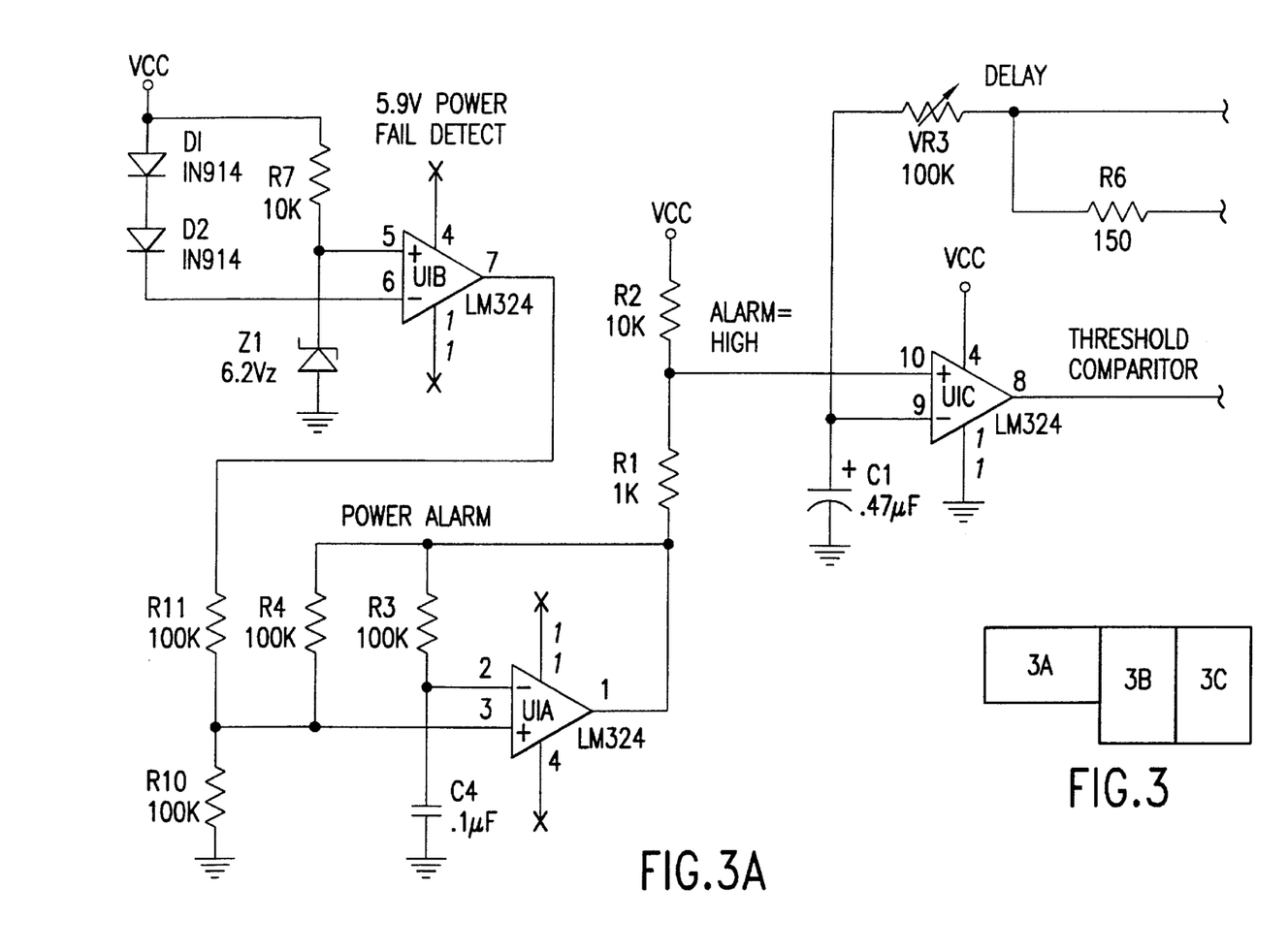
FIG. 3 is a schematic drawing of circuitry suitable to send a signal resulting from eyelid movement.
Figure 3B:
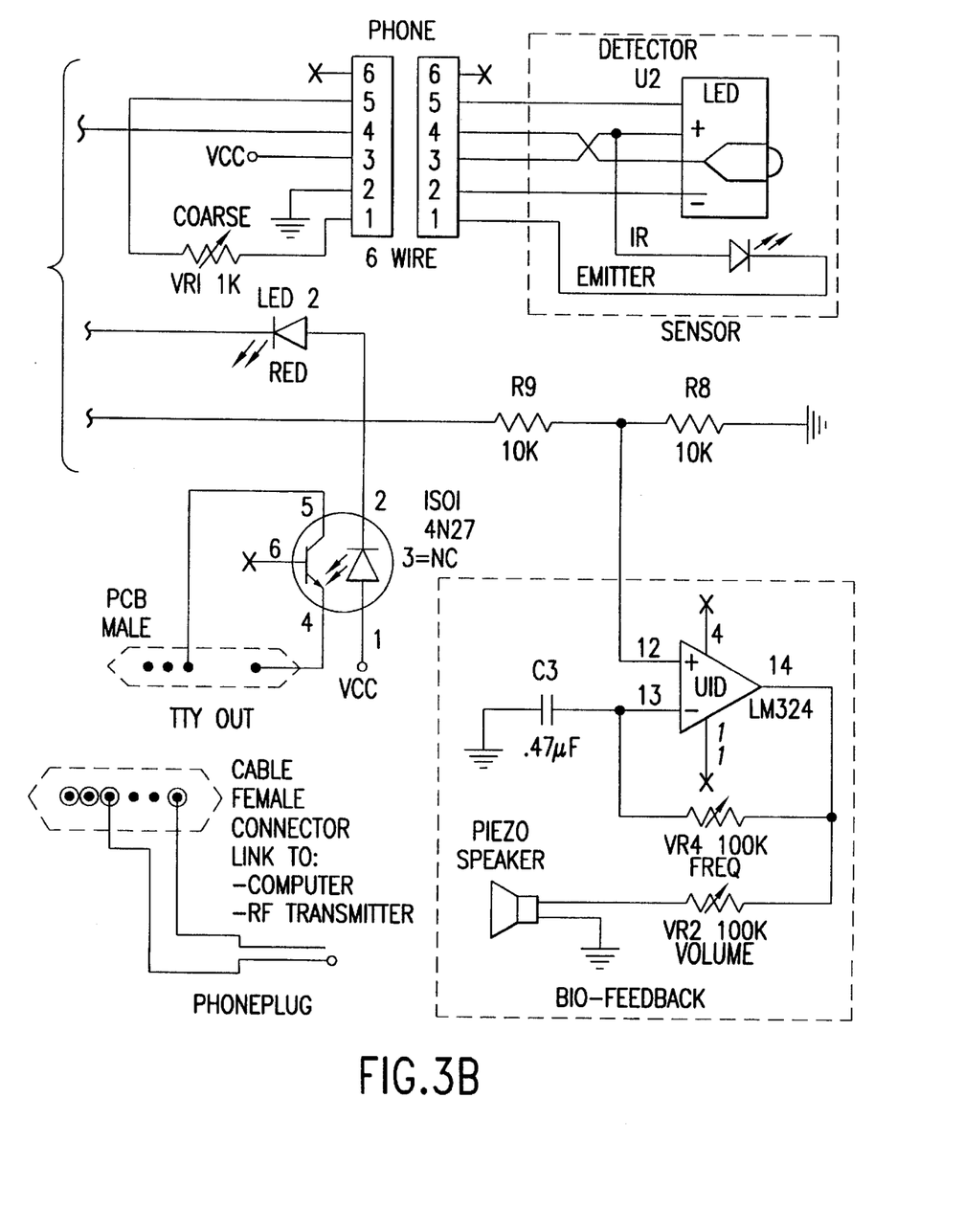
Figure 3C:
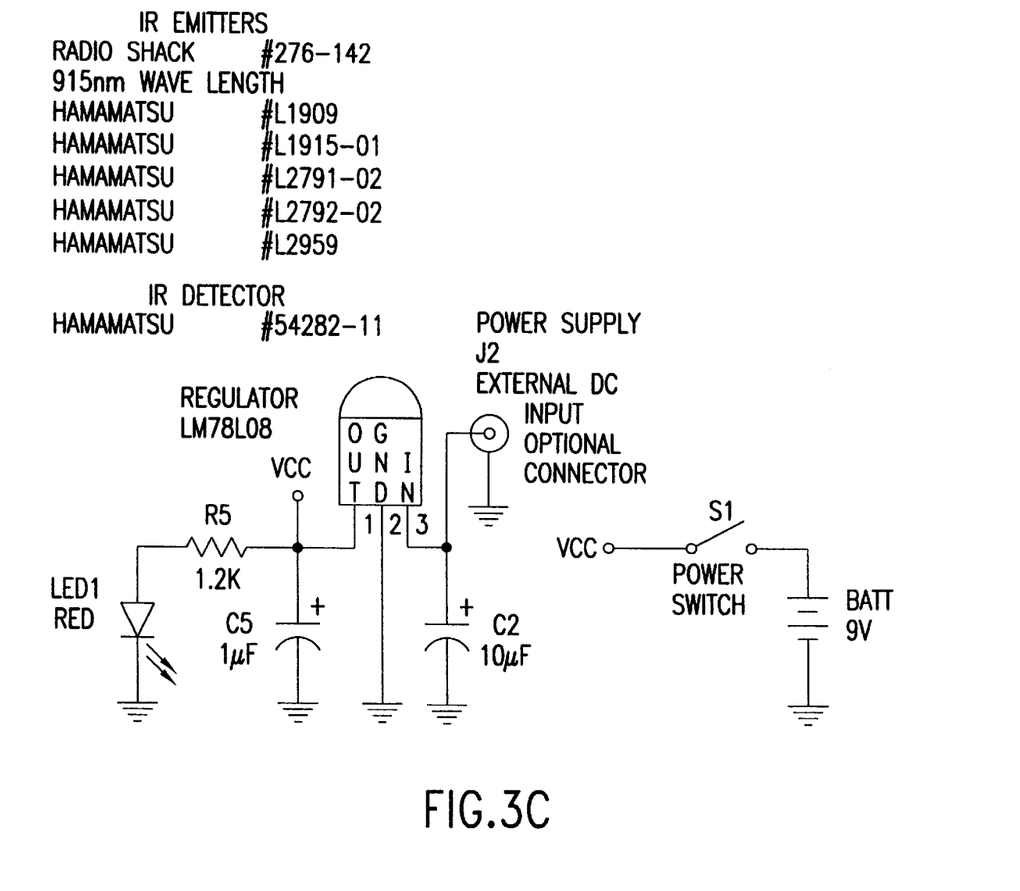

FIG. 3 needs no further explanation, as this merely is an example of a circuitry, understood by those skilled in the art, suitable to transmit a signal detected from eyelid movement.

Figure 4:
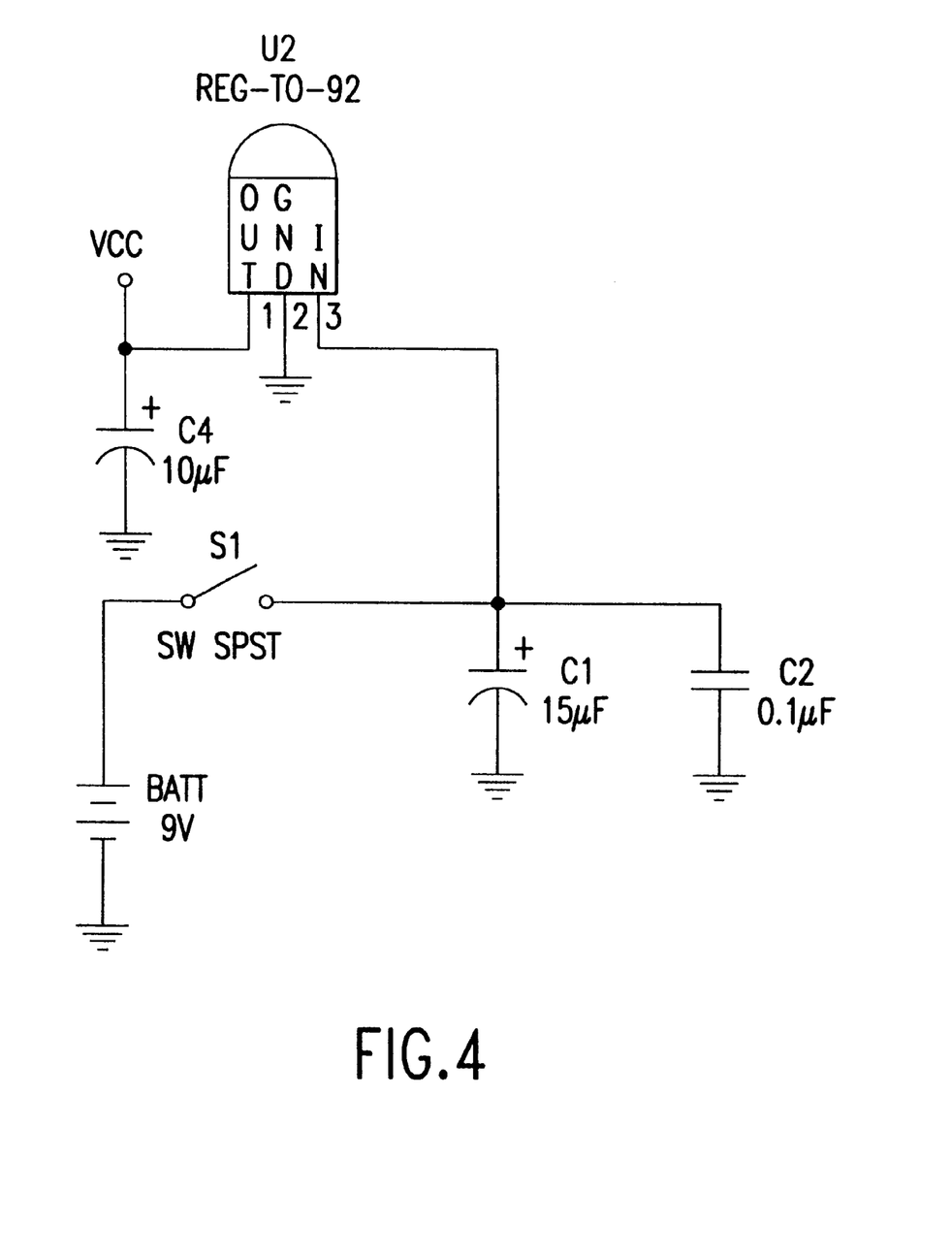
FIG. 4 is a schematic drawing of circuitry to control other equipment based upon the eyelid responses detected in practicing this invention.
Figure 4A:
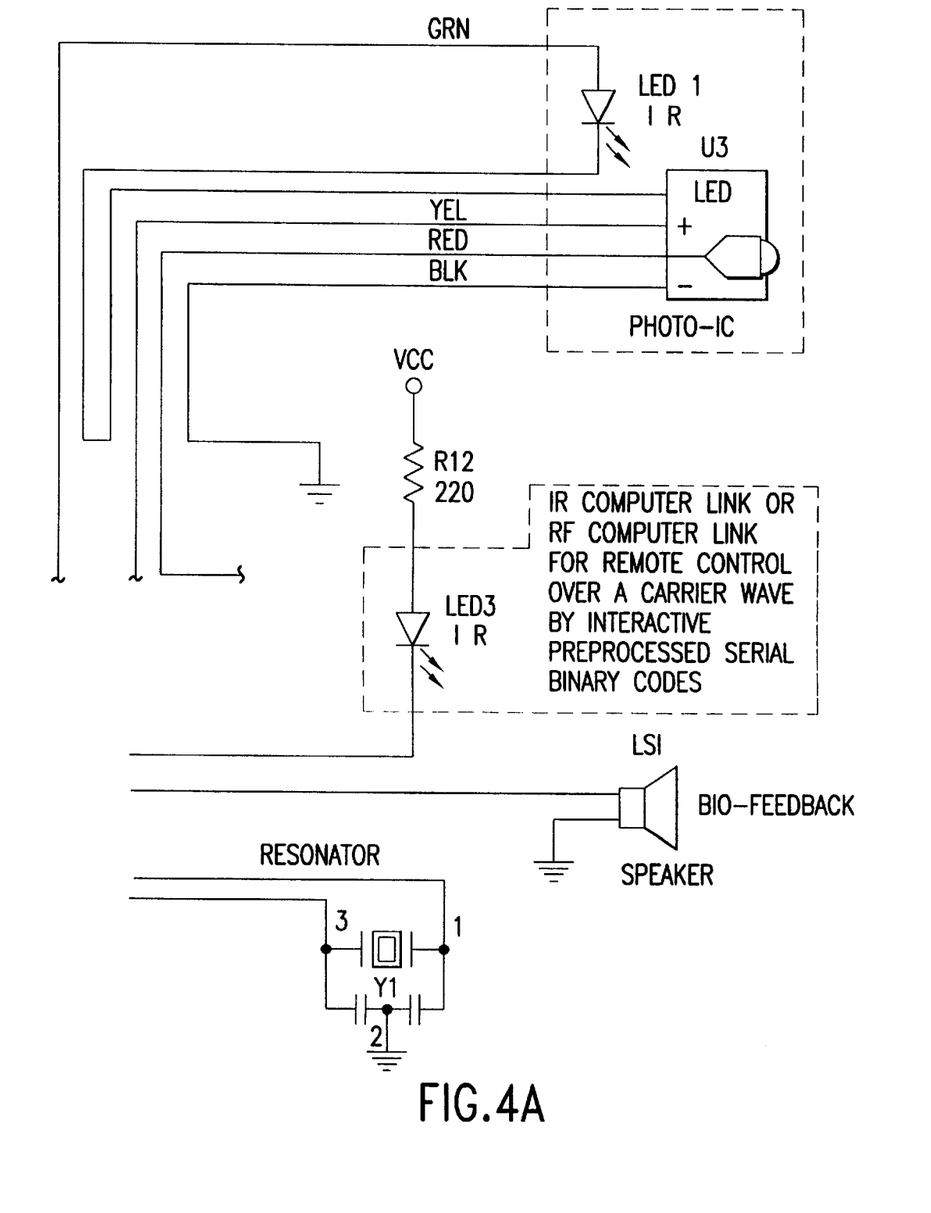
Figure 4B:
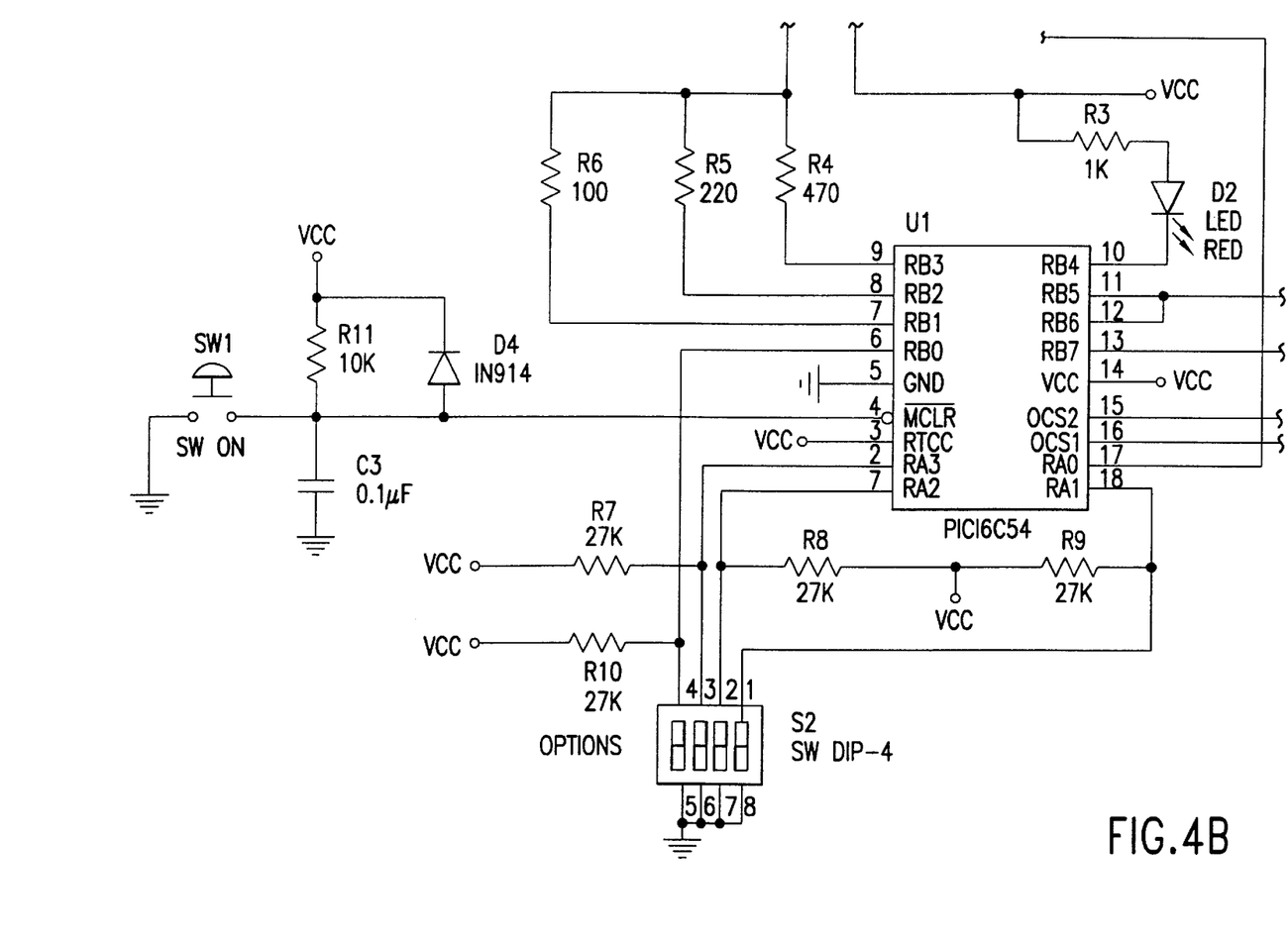

FIG. 4 is a circuitry, known to those skilled-in the art to control other apparatus (artificial voices, graphics, and the like). There are variations which will occur to those skilled in the art.

Figures 5, 5A:
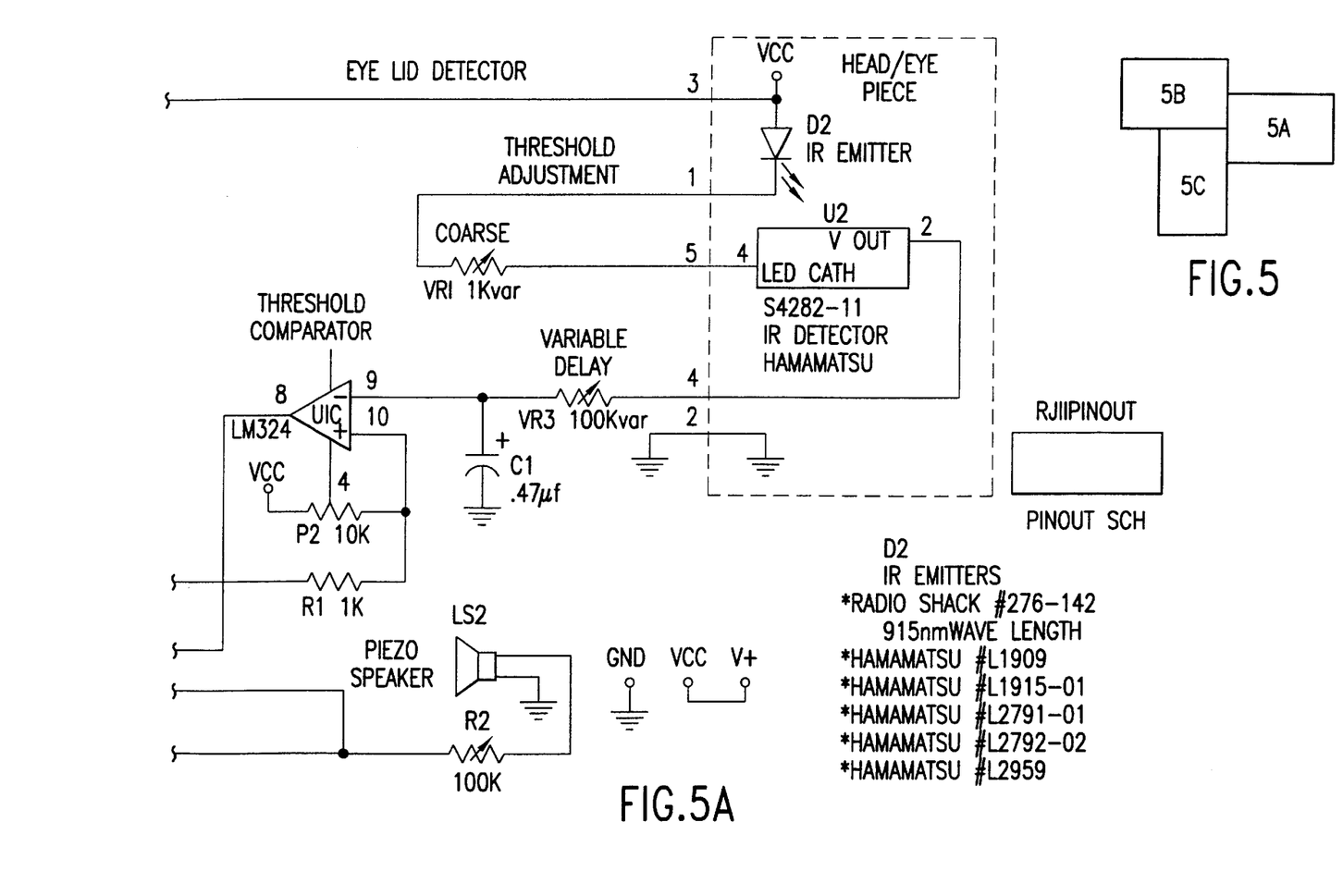
FIG. 5 is a schematic drawing of circuitry to actually detect the eyelid movement.
Figure 5B:
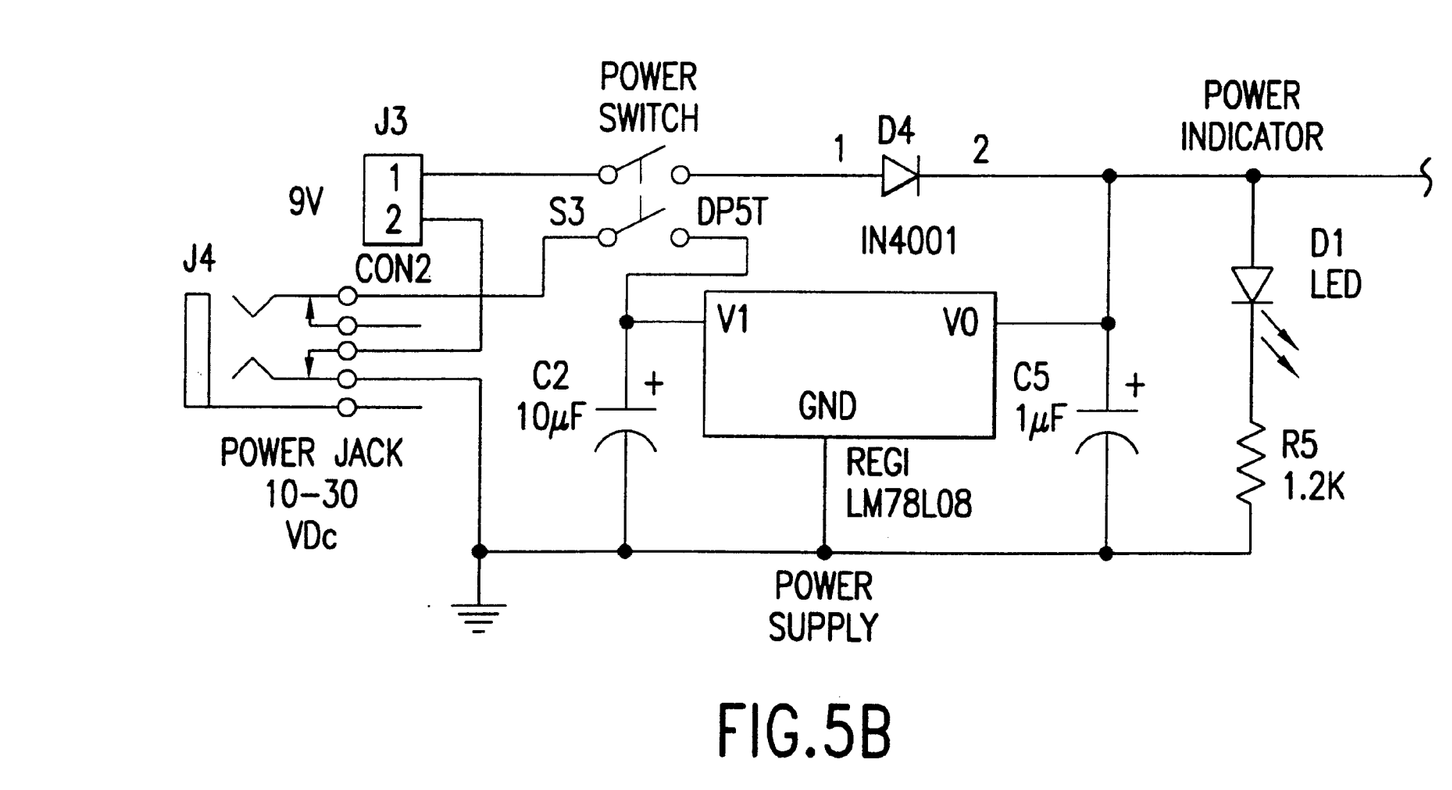
Figure 5C:
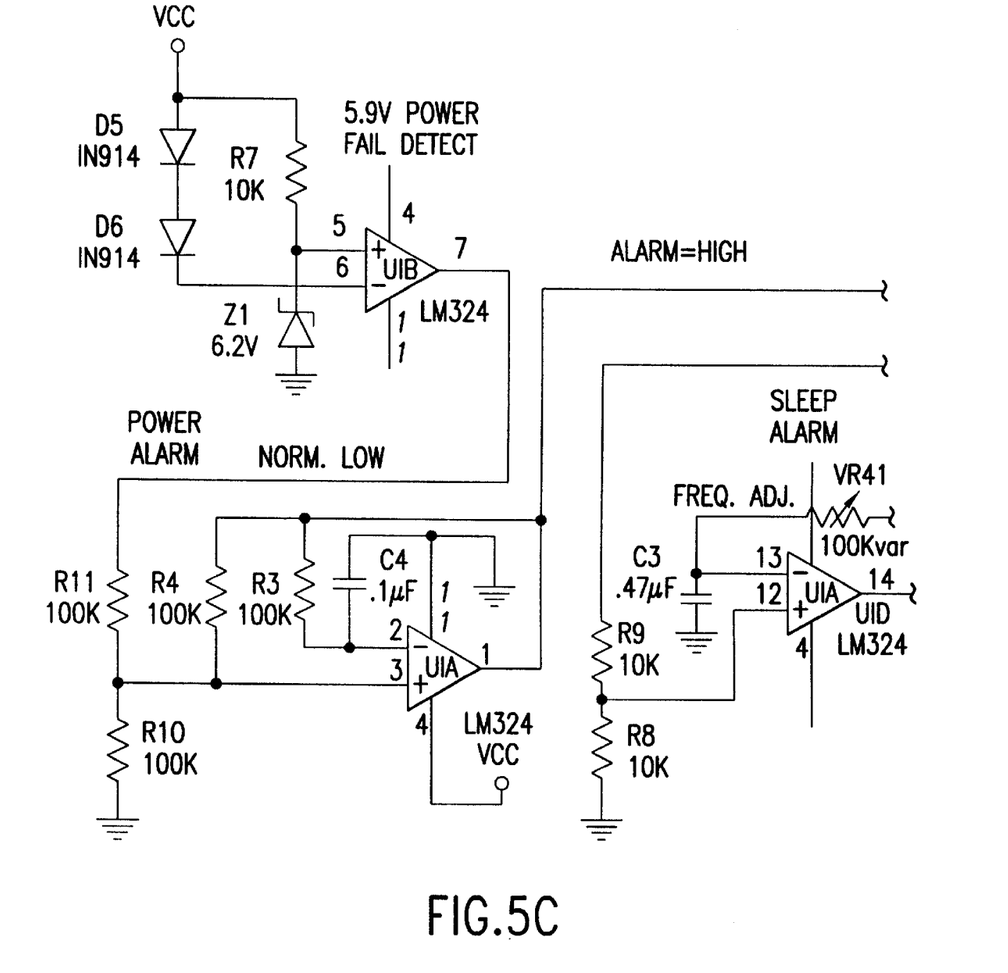

FIG. 5 is a circuitry, known to those skilled in the art utilized in actually detecting the eyelid movement. There could be various deviations, although it is believed this is very near the optimum for this purpose at the present state of the art.

Figure 6:
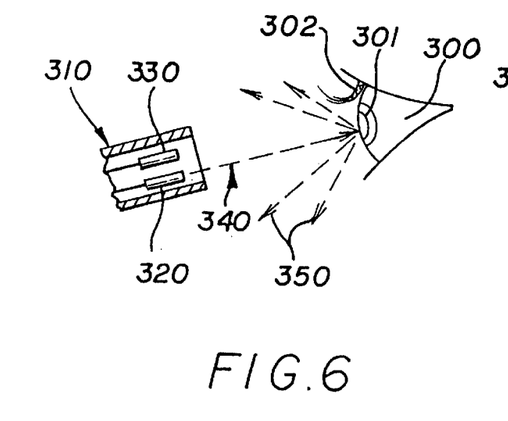
FIG. 6 is a schematic drawing of the method of detecting that an eyelid is open.
Figure 7:
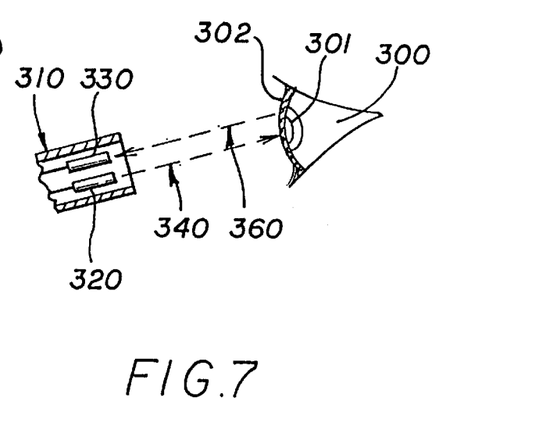
FIG. 7 is a schematic drawing as in FIG. 6, but showing the eyelid closed.

FIG. 6 shows the situation where the eyelid 302 is open. The emitter 320 send the signal 340 to the eye 300. The signal 340 is scattered as shown at 350 when it strikes the open eye 300 or the pupil 301. Thus the detector receives no return signal. In FIG. 7 the reverse situation is shown, where the eyelid 302 is closed. In the case of the closed eyelid, the signal 340 is reflected back to the detector as shown by the path 360.

Figure 8:
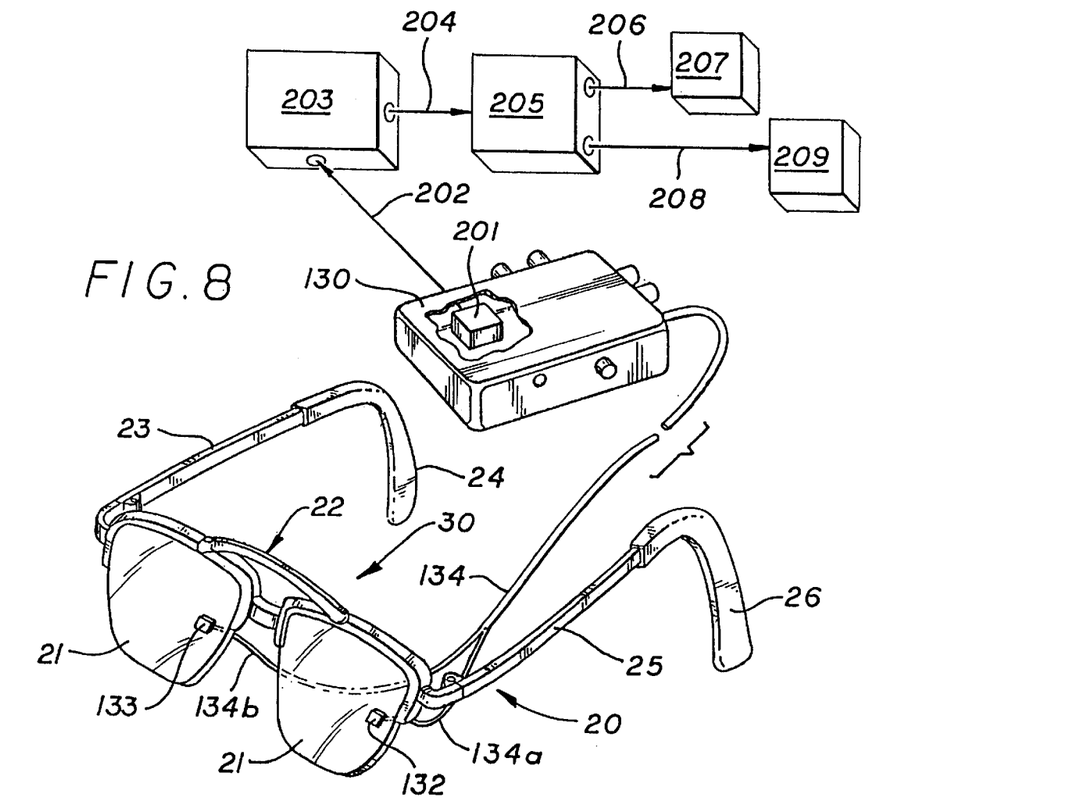
FIG. 8 is a schematic—perspective—block diagram showing alternate means to mount emitter/detectors on an eyeglass frame together with illustration of alternate read-out methods.

FIG. 8 illustrates alternate mountings for the light emitter/detectors 132 and 133 being carried by the eyeglasses of FIG. 2 and shows some of the ways the results of the use of this method may be displayed. In this case the emitter/detectors may be embedded within the actual eyeglass lenses 21, in the nasal bridge, or on the sides of the frame, etc. It should be noted that the sensor/emitter(s) may be carried by an eyeglass frame with or without actual eyeglass lenses being used. Leads 134, 134a, and 134b will carry the signals resulting from the detection/non-detection of the emitter signal by the detector to processing unit 130. Transmitting unit 201, within the processor 130 will transmit a radio frequency (note: the use of radio frequency is believed to be unique and inventive in itself, although it is not necessarily limited to such, as other signals may be used which would still be within the scope of this invention) signal 202 to a computer or the like 203, which will then transmit signal 204 to a further display processor 205 which will transmit signal 206 to a television or other monitor 207 for display, or to an audio or other (for example appliance switching devices; facsimile, telephone, radio, television, powered wheel chairs, vehicle alarms or analyzers, and a host of others) notification or utilization device 209 (for example, television monitor, analyzer, radio, lighting, telephone, alarm, electric powered wheelchair, electric powered hospital bed, etc.) by signal 208. All of these means for processing, display, switching and read-out are known to those skilled in the art, and, therefore, although such means are totally novel and unique in connection with my communication system disclosed, they are not described in detail here.

In using this method for communication, a person unable to communicate otherwise can respond to questions by blinking his eyelid. For example, one blink could mean "yes"; two blinks could mean "no"; three blinks could mean "I don't know". The combinations are unlimited, and, additionally a Morse code could be generated by a series of short blinks and long blinks. Another variation could be a blink of the left eye to mean a dot (in Morse code, or the like) and a blink of the right eye to mean a dash. Alternatively one blink, or one code signal generated by blinks could be used to represent a phrase, a word, a picture, a concept, or the like (examples would be "I need help."; "Robbery in progress."; "Please turn me over."; "I am in pain" "please change the television channel", and the like. In various combinations such a system could be suitable to create a new form of code or language.

An interesting application would be a binary code which could be transmitted directly to a computer, or the like and be immediately read out on a monitor, or converted to synthesized voice, or printed, or the like.

There are other possible uses, such as a silent signaling system for use in sensitive situations where it is desired to transmit emergency signals which cannot be detected by persons unaware of the signaling (examples could be bank tellers, security guards, prison guards, intelligence personnel, military operations, or the like).

Also, this new method of communication could be used to signal a sudden loss of consciousness, sudden onset of sleep, an epileptic fit characterized by involuntary closure of the eyelid. Under these situations the signal generated utilizing this method might trigger an emergency signal calling for the response of others who are capable of receiving the remote response signal.

I have used the term "light" in connection with the reflectiveness of the eyelid, and the eye itself. It is to be understood that certain other rays outside of the visible spectrum may be used to practice the method of this invention. Therefore, where the term "light" or "ray of light" is used in this application, including the descriptions and claims it is meant to include all types of rays and reflected rays, regardless of the wavelength or other characteristics.

While the embodiments herein illustrated and described are fully capable of achieving the objects and advantages of this invention, it must be understood that such embodiments are for purposes of illustration, only, and not for purposes of limitation, and, particularly in the face of rapidly developing technology, they are not to limited as to scope when considered with new technology.

I claim:

1. A method of communication of a voluntary human desire of a first human which includes: the first human imparting movement to at least one eyelid of the first human which movement is coded to indicate a mental desire or condition of the first person; detecting said eyelid movement by a detecting means; transmitting said detection to a detection recording means; recording the detection of the coded eyelid movement by said recording means; and observing said recording by a second human.

2. The method of claim 1 wherein the detection is based upon the relative reflectivity of the eyelid and the eyeball of the first human.

3. The method of communicating the mental desires of an individual comprising: moving at least one eyelid of the individual in a coded sequence by comparing the reflectivity of the eyeball and the eyelid; and decoding the detected coded sequence eyelid movement into a communication of the mental desires of the individual.

4. The method of claim 3 wherein the detection of eyelid movement is by means of light rays of a wavelength such that ambient light or other rays do not interfere with the detection.

5. A silent communication and signaling system comprising: means to detect eyelid movement of an individual in a coded sequence; means to transmit the detected eyelid movement to a remote location; and means to decode the detected coded movement into a meaningful message or action.

6. The system of claim 5 wherein the means to detect the eyelid movement includes rays of invisible wavelength.

* * * * *